United States Patent
Vogt et al.

(10) Patent No.: US 9,486,617 B2
(45) Date of Patent: Nov. 8, 2016

(54) ROTARY VALVE BODY FOR BONE CEMENT DISPENSING DEVICE

(71) Applicant: Heraeus Medical GmbH, Wehrheim (DE)

(72) Inventors: Sebastian Vogt, Erfurt (DE); Clemens Greiner, Garbsen (DE); Rudolf Hein, Neustadt (DE)

(73) Assignee: Heraeus Medical GmbH, Wehrheim (DE)

(*) Notice: Subject to any disclaimer, the term of this patent is extended or adjusted under 35 U.S.C. 154(b) by 150 days.

(21) Appl. No.: 14/029,008

(22) Filed: Sep. 17, 2013

(65) Prior Publication Data

US 2014/0077115 A1    Mar. 20, 2014

(30) Foreign Application Priority Data

Sep. 20, 2012 (DE) .......................... 10 2012 018 596

(51) Int. Cl.
*F16K 11/085* (2006.01)
*F16K 5/18* (2006.01)
*A61M 39/22* (2006.01)
(Continued)

(52) U.S. Cl.
CPC .......... *A61M 39/22* (2013.01); *A61B 17/8822* (2013.01); *A61B 17/8825* (2013.01); *A61B 17/8827* (2013.01); *F16K 5/0407* (2013.01); *F16K 11/085* (2013.01);
(Continued)

(58) Field of Classification Search
CPC ...... F16K 5/0407; F16K 5/045; F16K 5/184; F16K 11/085; F16K 11/0856

USPC ................. 137/625, 625.19, 625.22
See application file for complete search history.

(56) References Cited

U.S. PATENT DOCUMENTS 2,887,899 A * 5/1959 Urbas ............................. 74/545
3,224,462 A * 12/1965 Lopker .................... 137/625.19
(Continued)

FOREIGN PATENT DOCUMENTS

DE    102010019224 B3    10/2011
DE    102010019222 A1    11/2011
(Continued)

OTHER PUBLICATIONS

English Abstract of Uchida et al, JP 10009409 A, Jan. 1998, JPO/Derwent.*
(Continued)

*Primary Examiner* — Marina Tietjen
*Assistant Examiner* — Seth W Mackay-Smith
(74) *Attorney, Agent, or Firm* — Norris McLaughlin & Marcus, P.A.

(57) ABSTRACT

A rotary valve body for a dispensing device is arrangable in a matching valve seat in the dispensing device, whereby the rotary valve body is rotationally symmetrical about the rotation axis of the rotary valve body at least within a region intended for the valve seat. At least one sealing cam is arranged on the rotationally symmetrical jacket surface of said region and is raised above the radius of the rotationally symmetrical jacket surface such that the sealing cam renders the circumference of the rotary valve body larger than the internal diameter of the valve seat. At least one feed-through is arranged in the rotary valve body and extends from a first opening in the rotationally symmetrical jacket surface into a second opening in the rotationally symmetrical jacket surface.

20 Claims, 3 Drawing Sheets

(51) Int. Cl.
*A61B 17/88* (2006.01)
*F16K 5/04* (2006.01)
*A61B 17/00* (2006.01)

(52) U.S. Cl.
CPC ... *F16K 11/0856* (2013.01); *A61B 2017/0023* (2013.01); *Y10T 137/86566* (2015.04)

(56) References Cited

U.S. PATENT DOCUMENTS

| | | | |
|---|---|---|---|
| 4,328,833 A | 5/1982 | Aurther | |
| 5,477,884 A * | 12/1995 | Barkes | 137/625.41 |
| 5,544,854 A * | 8/1996 | Carroll | 251/99 |
| 6,240,959 B1 * | 6/2001 | Loper | 137/599.01 |
| 2006/0208000 A1 | 9/2006 | Murray | |
| 2011/0272437 A1 * | 11/2011 | Vogt et al. | 222/389 |
| 2011/0272438 A1 | 11/2011 | Vogt et al. | |
| 2013/0115111 A1 | 5/2013 | Wust et al. | |

FOREIGN PATENT DOCUMENTS

| | | |
|---|---|---|
| EP | 1607694 A1 | 12/2005 |
| EP | 2267345 A2 | 12/2010 |
| JP | 10009409 A * | 1/1998 ............... F16K 5/04 |
| JP | H109409 A | 1/1998 |

OTHER PUBLICATIONS

Japanese Office Action for corresponding Japanese Application No. JP 2013-191592 dated May 12, 2015.
European Examination Report for corresponding European Application No. EP 1318 1138.2 dated Jan. 7, 2014.

* cited by examiner

ROTARY VALVE BODY FOR BONE CEMENT DISPENSING DEVICE

The invention relates to rotary valve bodies for bone cement dispensing facilities. Another object of the invention is a rotary valve that is inexpensive in production and is designed to regulate the pressurised gas flow in pressurised gas-driven medical devices, whereby the medical devices made of plastic material are designed for single use.

PMMA bone cements are in frequent use for mechanical fixation of articular endoprostheses in orthopaedics and accident surgery. In modern vacuum mixing systems, the cement is produced inside a cartridge through mixing the polymer powder with the monomer liquid. The cement dough thus produced is subsequently expelled from the cartridge and applied by means of a hand-operated expelling device. The manual expelling process is considered to be unpleasant by many users because of the manual force it requires. For this reason, DE 10 2010 019 222 A1 and DE 10 2010 019 224 B3 proposed pressurised gas-driven expelling devices. Said devices are preferably made from inexpensive plastic material and designed for single use only. A rotary valve in said devices was proposed generally.

Moreover, DE 10 2012 013 464, which has not been pre-published, proposed rotary valves also in pressurised gas-driven spraying devices and in devices for short-term vacuum generation (DE 10 2011 117 527), which has not been pre-published) though no detailed description of the rotary valves was provided.

Pressures of up to 60 bar may be present where liquid carbon dioxide is used and thus far only expensive valves manufactured from metal are customary for regulation of pressures this high. Said valves are designed for a long service life and for providing several thousand opening and closing processes. Due to the high procurement costs, it is unreasonable and economically untenable to use valves made of metal for single-use applications involving few opening and closing processes.

Accordingly, it is the object of the invention to overcome the disadvantages of the prior art. Specifically, an inexpensive rotary valve is to be provided that can be manufactured inexpensively and whereby the rotary valve body preferably shall consist of a single part only. The rotary valve should be storable and its function should be driven by a pressurised gas at a pressure of 60 bar for up to 30 minutes. The rotary valve should have one switching position, in which a flow of pressurised gas can be blocked, and a second switching position, in which the flow of pressurised gas can flow.

It is another object of the invention to provide a rotary valve that attains not only regulation of a pressurised gas flow, but also synchronous pressure relief in the region of the recipient side of the rotary valve when the gas flow is blocked.

One insight according to the invention is that the high procurement costs make it is unreasonable and economically untenable to use valves made of metal for single-use applications involving few opening and closing processes.

The object of the invention was therefore met by a rotary valve body for a bone cement dispensing device that can be arranged in rotatable manner in a matching valve seat in the dispensing device, whereby the rotary valve body is rotationally symmetrical about the rotation axis of the rotary valve body at least within a region intended for the valve seat, and in that at least one sealing cam made of an elastic plastic material is arranged on the rotationally symmetrical jacket surface of said region and is raised above the radius of the rotationally symmetrical jacket surface such that the sealing cam renders the circumference of the rotary valve body larger than the internal diameter of the valve seat, and whereby at least one feed-through is arranged in the rotary valve body and extends from a first opening in the rotationally symmetrical jacket surface of the rotary valve body in the region of the sealing cam into a second opening in the rotationally symmetrical jacket surface of the rotary valve body.

In this context, the invention can provide at least a second sealing cam made of an elastic plastic material to be arranged on the rotationally symmetrical jacket surface and to be raised above the radius of the rotationally symmetrical jacket surface such that the second sealing cam renders the circumference of the rotary valve body larger than the internal diameter of the valve seat, and whereby at least a second feed-through is arranged in the rotary valve body, whereby the second feed-through extends from a third opening in the rotationally symmetrical jacket surface of the rotary valve body in the region of the second sealing cam into a fourth opening in the cover surface of the rotary valve body that is oriented outward with respect to the dispensing device.

A rotary valve body of this type is advantageous in that the second sealing cam enables a gas conduit for relieving an overpressure from the dispensing device. By this means the pressure acting on a feed plunger can be taken off in order to interrupt further dispensation of a medical fluid, such as a bone cement.

Moreover, the invention can provide the entire rotary valve body to be made of more than 90% plastic material, preferably to be completely made of plastic material, preferably of the same plastic material as the sealing cam or sealing cams, whereby the rotary valve body and the sealing cam or sealing cams particularly preferably are made up of a single part.

This allows a particularly inexpensive production of the rotary valve body to be attained.

According to a refinement, the invention can also provide the sealing cam or sealing cams to consist of polyoxymethylene, polyamide or TEFLON (polytetrafluoroethylene (hereinafter PTFE))and, preferably, the rotary valve body to also be made of more than 90%, preferably to be completely made of, polyoxymethylene, polyamide or TEFLON (PTFE).

It is particularly preferable to use polyoxymethylene as material for the sealing cam and particularly preferably for the rotary valve body as well. Polyoxymethylene and the other materials as well possess a particularly well-suited elasticity such that the sealing cam or sealing cams can reliably close an opening in gas-tight manner by means of the elastic pressure even if an over-pressure is applied to the sealing cam.

According to another preferred embodiment, the invention can provide the first opening to be arranged at the same height, with respect to the rotary axis of the rotary valve body, as the first sealing cam, and, preferably, the third opening to be arranged at the same height, with respect to the rotary axis of the rotary valve body, as the second sealing cam.

This enables the valve seat into which the rotary valve body is to be inserted to be simple in design.

The invention can just as well provide the first feed-through to extend through the rotary valve body such as to be perpendicular to the rotary axis of the rotary valve body such that the first opening becomes arranged opposite to the second opening.

Since the two openings are situated at a large distance from each other, the inserted rotary valve body can be very tight.

Moreover, the invention can provide an axial hollow space to be arranged in at least one of the cover surfaces of the rotary valve body and to be open towards the outside, whereby the fourth opening is arranged in the hollow space, whereby the hollow space is preferably arranged in the cover surface of the rotary valve body facing outward with respect to the dispensing device.

Having this hollow space allows much material to be saved such that the design of the rotary valve body becomes simpler and less expensive.

According to a further preferred embodiment, the invention provides at least two tangentially circumferential grooves in the rotationally symmetrical jacket surface of the rotary valve body, whereby it is preferable that guide rings, particularly preferably plastic guide rings, are arranged in the grooves.

The grooves enable the rotary valve to be sealed while the rotary valve body is inserted in the valve seat. Moreover, the guide rings serve to guide the rotation of the rotary valve body in the valve seat.

Referring to rotary valve bodies according to the invention having two feed-throughs, the invention can preferably provide the first opening and the third opening to be offset with respect to each other by at least 10° relative to the rotation axis of the rotary valve body and to be arranged at different height, in particular to be arranged offset by between 10° and 90° with respect to each other.

This ensures sufficient rotation of the valve body to enable easy and reliable operation of the rotary valve.

Referring to rotary valve bodies with two feed-throughs of this type, the invention can further provide the first sealing cam and the second sealing cam to be offset with respect to each other by at least 10° relative to the rotation axis of the rotary valve body and to be arranged at different height, in particular to be arranged offset by between 15° and 90° with respect to each other, whereby the first sealing cam is preferably arranged at the same height with respect to the rotation axis as the first opening, the second sealing cam is preferably arranged at the same height with respect to the rotation axis as the third opening, and the sealing cams are offset with respect to the openings arranged at the same height by the same angle by which the sealing cams are offset with respect to each other.

Said arrangement of sealing cams and openings with respect to each other allows the dispensing device having gas conduits to be designed particularly simply, since the gas conduits of the dispensing device open next to each other into the valve seat and since ventilation and the application of pressure are feasible by means of a slight rotation of the valve body in the valve seat.

Preferably, the invention can provide the cover surface of the rotary valve body facing outwards with respect to the dispensing device has at least one key element arranged in it that is not symmetrical to the rotation axis of the rotary valve body such that the rotary valve body can be rotated in the valve seat by means of an operating element that engages the key element in form-fitting manner.

Having this key element allows to ensure that the valve made up of the rotary valve body is simple and safe to operate.

In this context, the invention can provide the key surface to be triangular, square, rectangular, hexagonal, octagonal or ellipsoidal in shape or to be formed from a combination of squares, rectangles, triangles, ellipses or circles.

This allows a simple operating element to be inserted that can be used intuitively right away and at the same time provides a stable connection between the operating element and the key surface.

The objects of the invention are also met by a valve system comprising a rotary valve body of this type and a valve seat, in which the rotary valve body is supported like in a bearing such that it can rotate, whereby the sealing cam or sealing cams of the rotary valve body are compressed by the valve seat.

In this context, the invention can provide the valve seat to be manufactured from plastic material, preferably from thermoplastic material, particularly preferably from polyamide, polyetherketone and/or polyimide.

Due to this design, the entire valve consisting of valve seat and rotary valve body can be manufactured from inexpensive materials.

Moreover, the invention can provide for at least two, preferably at least three, openings opening into gas conduits to be arranged in the valve seat, whereby a sealing cam closes at least one opening in a first position of the rotary valve body in the valve seat and, in a second, rotated, position of the rotary valve body in the valve seat, the feed-through connects at least two openings such that a through-going gas conduit is formed.

This design ensures trouble-free operability and handling of the final rotary valve.

According to a preferred refinement of the valve, the invention can provide in the valve seat at least three openings opening into gas conduits, whereby the first sealing cam, in a first position of the rotary valve body in the valve seat, closes at least one opening and, in a second, rotated position of the rotary valve body in the valve seat, the feed-through connects at least two openings such that a through-going gas conduit is formed, and, in the first position, the third opening of the rotary valve body is connected to one of the openings in the valve seat and, in the second, rotated position of the rotary valve body in the valve seat, the second sealing cam closes said opening in the valve seat.

These measures also serve to improve the functioning of the rotary valve in its final design.

And lastly, the objects on which the invention is based are also met by a medical dispensing device for single-use, in particular pressurised gas-driven medical bone cement dispensing device, spraying device or vacuum-generating device having a valve system of this type for regulating the gas flow.

The invention is based on the surprising finding that the use of elastic sealing cams allows an inexpensive rotary valve body to be designed that can be used to implement pressure-tight sealing of gas conduits for compressed gases. For this purpose, the flexible elastic sealing cams seal the openings into which the gas conduits of an expelling device open even against pressures that may occur during the use of $CO_2$ cartridges.

In order not to generate excessive pressures, the invention can provide an overpressure valve that opens from a certain predetermined pressure. A pressure of 50 bar, for example, can be used as predetermined pressure.

The scope of the invention also includes a rotary valve having a valve seat regions of which are cylindrical, whereby the rotary valve body comprises the following features:

a) a cylindrical base body;
b) a gas-permeable opening that extends through the cylinder such as to be perpendicular to the jacket surface of the cylinder;

c) a sealing cam that is arranged on the external jacket surface and is raised above the external diameter of the cylinder and is arranged adjacent to the opening at the same distance as that between the opening and the front face of the cylinder, whereby the external diameter of the sealing cam is larger than the internal diameter of the valve seat;

d) at least one key surface that is arranged on the front faces of the cylinder and can be connected to at least one operating element.

The scope of the invention also includes a rotary valve having a cylindrical valve seat, whereby the rotary valve body is made up of a) a cylinder having at least one axial hollow space that originates on one front face of the cylinder and is connected to the surroundings in gas-permeable manner;

b) at least two grooves extending tangentially circumferential on the external cylinder surface;

c) at least two guide rings that are arranged in the grooves;

d) a gas-permeable first opening that extends through the cylinder such as to be perpendicular to the jacket surface of the cylinder;

e) a gas-permeable second opening that connects the external jacket surface to the axial hollow space in gas-permeable manner;

f) a first sealing cam that is arranged on the external jacket surface and is raised above the external diameter of the cylinder and is arranged adjacent to the first opening at the same distance as that between the first opening and the front face of the cylinder, whereby the external diameter of the first sealing cam is larger than the internal diameter of the valve seat;

g) a second sealing cam that is arranged on the external jacket surface and is raised above the external diameter of the cylinder and is arranged adjacent to the second opening at the same distance as that between the second opening and the front face of the cylinder, whereby the external diameter of the second sealing cam is larger than the internal diameter of the valve seat;

h) whereby the openings are offset by a minimal angle of 10°;

i) whereby the sealing cams are offset by a minimal angle of 10°;

j) whereby the openings are arranged to be diagonal with respect to each other;

k) whereby the sealing cams are arranged to be diagonal with respect to each other;

l) whereby the diagonal between the openings intersects the diagonal of the sealing cams in such manner that the distances of the openings to the point of interception and the distance of the sealing cams to the point of interception are equal in length; and m) in that at least one key surface that can be connected to at least one operating element is arranged at the front faces of the cylinder.

The invention can also provide for the entire surface of the sealing cams to be a section of a jacket surface of a cylinder that has a larger external diameter than the cylinder. The external diameter of the sealing cams is smaller than the internal diameter of the valve seat. Due to the surface of the sealing cams being circular, the sealing cam surface is sufficiently smooth to not only provide the sealing function, but also to provide for sliding along the valve seat. Since the external diameter of the sealing cams is larger with respect to the cylinder, the cam surface is being pressed against the valve seat. Only this contact pressure ensures that effective sealing can be attained even at gas pressures of 60 bar as occur when liquid carbon dioxide is used.

The scope of the invention further includes a key surface that is connected to the operating element in a form-fitting manner to be provided on the valve body. This means that a motion of the operating element, for example a trigger handle, can be transferred to the valve element by the form-fit with the key element such that the valve element is being rotated in the valve seat and the pressurised gas flow can thus be switched on and off.

Referring to the key surface of the present invention, it is important that the motion of the operating element is transferred to the valve element without any slippage. For this reason, the shape of the key surface should be designed appropriately to prevent any slippage.

The key surface can therefore be triangular, square, rectangular, hexagonal, octagonal or ellipsoidal in shape. It is feasible just as well to form key surfaces from combinations of squares, rectangles, triangles, ellipses or circles.

The scope of the invention also includes that the valve seat and the valve body preferably consist of plastic material, whereby thermoplastic material is particularly preferred. This allows the valve to be manufactured inexpensively through injection moulding.

The valve seat preferably consists of rigid polymers showing very little creepage. Polyamide, polyetherketone, and polyimide are preferred in this context. Polyamide 12 has proven to be particularly well-suited for this purpose.

The rotary valve also consists of a plastic material. Polyoxymethylene, polyamide, and TEFLON (PTFE) have proven to be well-suited in this context. Polyoxymethylene is particularly well-suited, since this polymer possesses very high dimensional stability and, on the other hand, sufficiently strong resilience. Another advantage of polyoxymethylene is its negligible creepage. Moreover, polyoxymethylene shows very good friction behaviour. For this reason, polyoxymethylene is particularly preferred for manufacturing the sealing cams or the entire rotary valve.

The rotary valve is intended for regulation of the gas flow in medical devices, in particular in dispensing devices for bone cement for single use. Conceivable medical devices are, in particular, expelling devices according to DE 10 2010 019 222 A1 and DE 10 2010 019 224 B3, spraying devices (as DE 10 2012 013 464, which has not been prepublished), and devices for generation of a temporary vacuum (as DE 10 2011 117 527, which has not been prepublished), whereby the device-specific features of the medical devices are herewith included expressly by way of reference.

Exemplary embodiments of the invention shall be illustrated in the following on the basis of six schematic figures, though without limiting the scope of the invention. In the figures.

Figure 1:
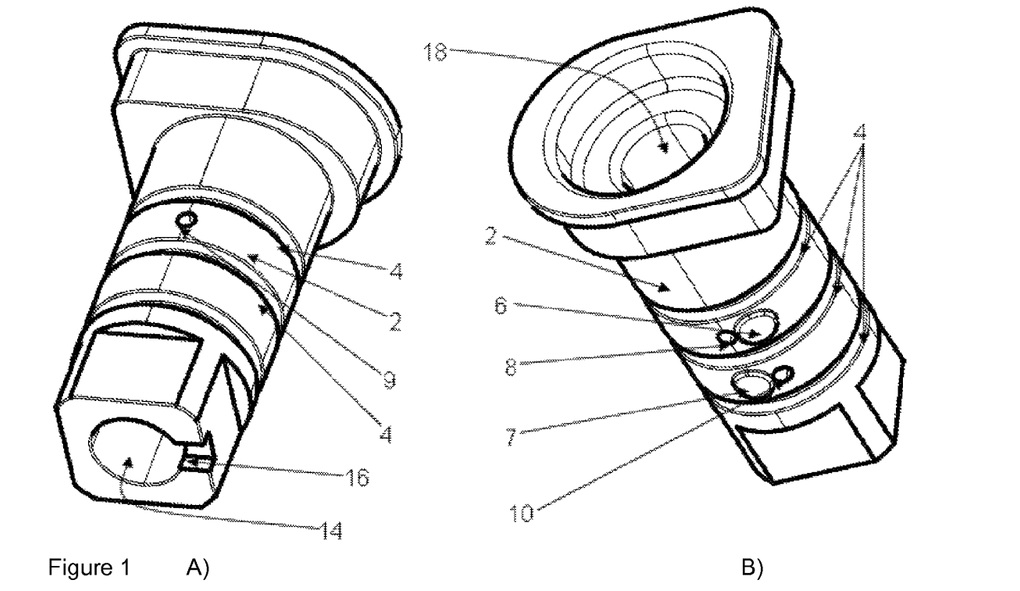
FIG. 1: shows two schematic perspective side views from opposite sides of a rotary valve body according to the invention.

FIG. 1 shows two schematic perspective side views from opposite sides of a rotary valve body according to the invention. The rotary valve body comprises a cylindrical jacket surface 2 which is to touch against a valve seat of a medical dispensing device in its assembled state (not shown). Grooves 4 are arranged in the cylindrical jacket surface 2 and are provided to accommodate guide rings that are used to position the rotary valve body in the valve seat during the rotation. The guide rings can just as well be firmly connected to the valve seat.

The cylindrical jacket surface 2 can just as well be designed to be slightly conical in shape. A first sealing cam 6 and a second sealing cam 7 made of polyoxymethylene are arranged between the grooves 4 on the jacket surfaces 2. In the assembled state, these serve to close, in gas-tight manner, the openings of two gas conduits in the valve seat as a function of the rotation of the rotary valve body.

A first opening 8 is arranged adjacent to the first sealing cam 6 and opens into a passage and extends to the rear side of the rotary valve body (FIG. 1 A), where it opens into a second opening 9 in the jacket surface 2 on the opposite side of the rotary valve body. A third opening 10 is arranged adjacent to the second sealing cam 7. It connects a passage to a fourth opening (not shown in FIGS. 1A) and 1 B)) that is arranged in a hollow space 14 of the rotary valve body. A recess 16 is arranged in one of the walls of the hollow space 14.

The cylinder axis of the cylindrical jacket surfaces 2 is the rotation axis of the rotary valve. The first sealing cam 6 and the first opening 8 are arranged at the same height with respect to said rotation axis. Likewise, the second sealing cam 7 and the third opening 10 are arranged at the same height with respect to the rotation axis of the rotary valve. The first sealing cam 6 and the first opening 8, much like the second sealing cam 7 and the third opening 10, are offset by 10° with respect to each other relative to the rotation axis of the rotary valve.

A second hollow space 18 is arranged on the front face of the rotary valve body opposite from the hollow space 14. The two ends in the region of the front faces of the rotary valve body possess broken rotational symmetry and can thus serve as key elements for operating elements.

Figure 2:
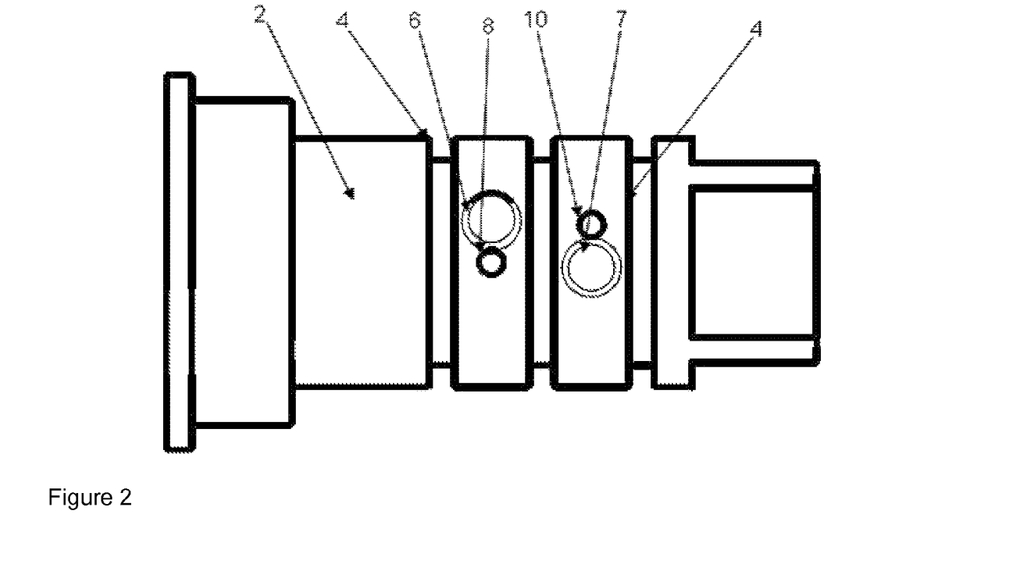
FIG. 2: shows a side view of a rotary valve body according to the invention.
Figure 3:
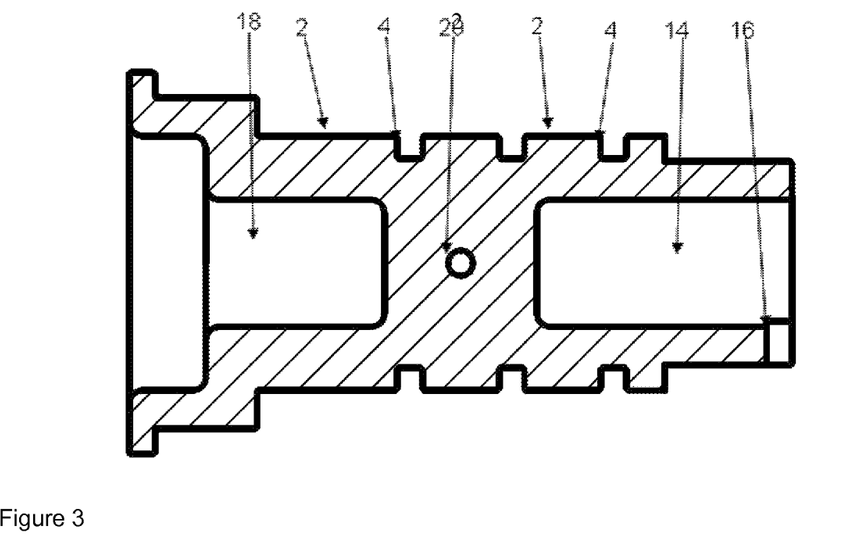
FIG. 3: shows a cross-sectional view along the rotation axis of a rotary valve body according to the invention.
Figure 4:
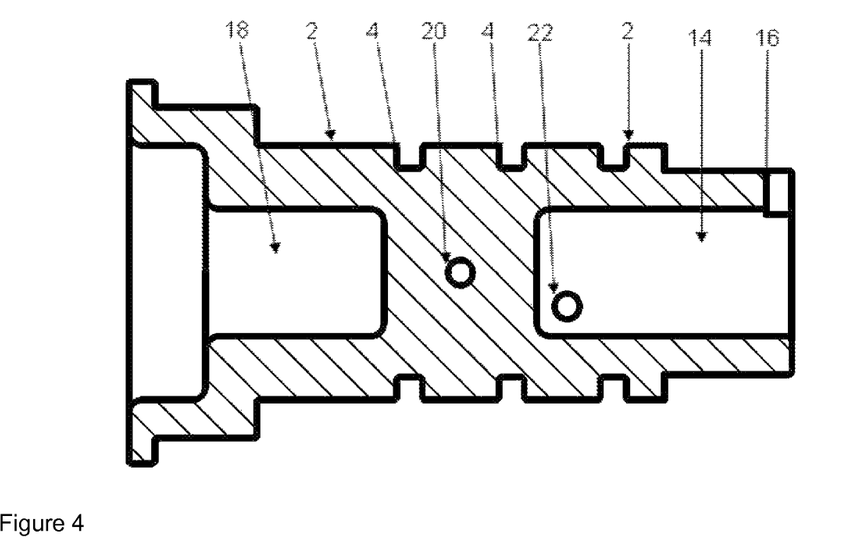
FIG. 4: shows a cross-sectional view along the rotation axis of a rotary valve body according to the invention in a direction opposite to that of FIG. 3.

FIG. 2 shows a side view of the rotary valve body according to the invention according to FIG. 1. FIGS. 3 and 4 show cross-sectional views along the rotation axis of the rotary valve body. They show, on the inside of the rotary valve body, the feed-through 20 that extends through the rotary valve body and connects the first opening 8 to the second opening 9. Moreover, FIG. 4 shows the fourth opening 22 in the first hollow space 14.

Figure 5:
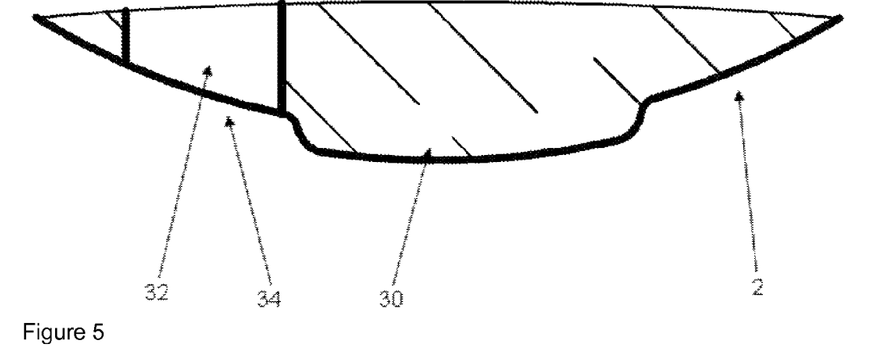
FIG. 5: shows a schematic cross-sectional view through a sealing cam and the adjoining regions of a rotary valve body according to the invention.

FIG. 5 shows a schematic cross-sectional view through a sealing cam 30 and the adjoining regions of a rotary valve body according to the invention in a sectioned view. An opening 34 is arranged adjacent to the sealing cam 30 and opens into a feed-through 34. The sealing cam 30 and the rotary valve body are provided as a single part made of a flexible plastic material. The sealing cam 30 is raised but slightly above the diameter of the rotationally symmetrical jacket of the rotary valve body on which the sealing cam 30 is arranged. In the valve seat, said sealing cam is compressed by the valve seat and serves to close an opening in the valve seat in pressure-tight manner.

Figure 6:
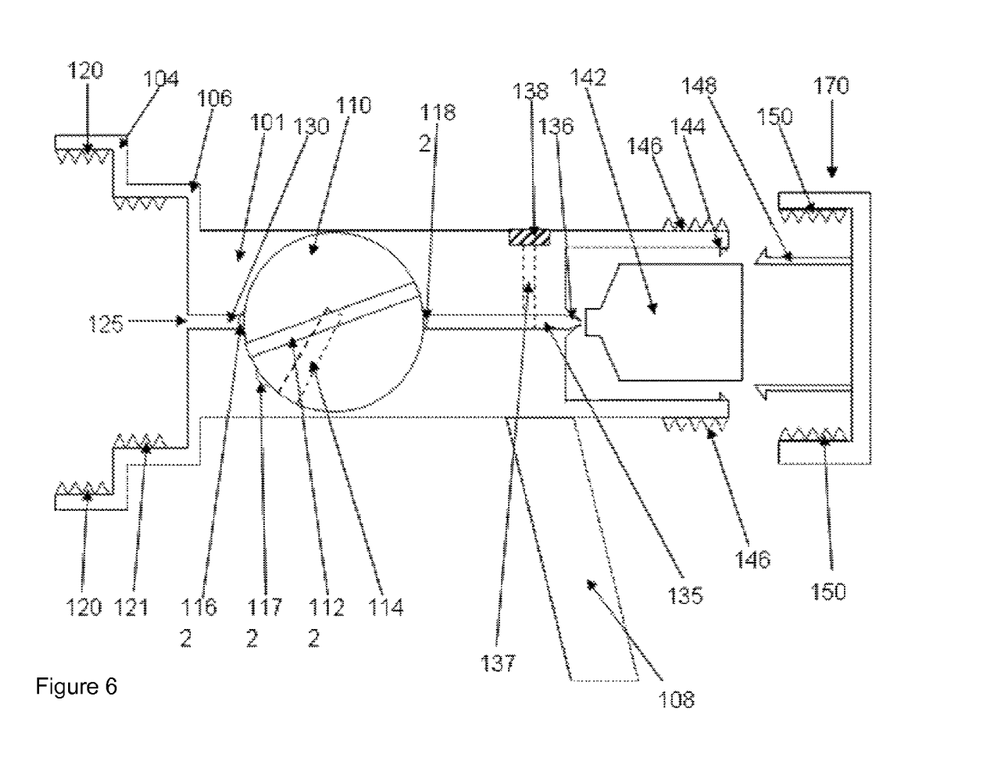
FIG. 6: shows a schematic cross-sectional view of a dispensing device according to the invention having a rotary valve according to the invention.

FIG. 6 shows a cross-sectional view of a dispensing device according to the invention having a base body 101 that has a first cartridge connector 104 having a large diameter for cartridges with a large diameter and a second cartridge connector 106 having a smaller diameter for cartridges with a smaller diameter being arranged on its front side. The internal cylinder walls of the cartridge connector parts 104, 106 have fixation devices 120, 121 in the form of internal threads provided on them for fixing in place cartridges with external threads (not shown). The fixation devices 120, 121 can just as well be implemented through threads, thread sections or pegs for locking the cartridges in the cartridge connectors 104, 106.

Three openings 125 leading to three passages in the base body 101 are situated in the rear wall of the second, inner cartridge connector 106. Cartridges that are fixed in place in the cartridge connectors 104, 106 seal tightly against the cartridge connectors 104, 106. This ensures that a gas pressure that is directed through one of the openings 125 to the floor of a fixed cartridge can actually act on said cartridge floor and does not escape between the cartridges and the cartridge connectors 104, 106. For this purpose, sealing elements (not shown) can be provided in the cartridge connectors 104, 106 and/or on the cartridges, in particular on the cartridge floors. However, it may also be sufficient to provide a sealed fixation device 120, 121 which can be implemented through a thread, for example.

A rotary valve body 110 showing rotationally-symmetrical geometry is situated in an opening in the base body 101 and is mounted in the base body 101 such as to be rotatable about its axis of symmetry (perpendicular to the sectional plane shown in FIG. 6). A first passage 112 is situated in the valve body and extends straight through the rotary valve body 110 and a second passage 114 that is angled and opens towards the outside in a front face of the rotary valve body 110 through a sterile filter (not shown) is situated in the valve body. Sealing cams 116, 117, 118 are situated at an offset of 20° with respect to the openings of the passages 112, 114 in the cylinder jacket of the rotary valve body 110.

A front gas conduit 130 is arranged in the front part of the base body 101 (facing the cartridge connectors 104, 106) and opens into an opening 125 towards the cartridge connectors 104, 106.

Two rear gas conduits 135 that open into openings towards the rotary valve body 110 are arranged in the rear part of the base body 101. The sealing cams 116, 117, 118 can be used to close the openings towards the gas conduits 130, 135 in the valve seat of the rotary valve 110 in gas-tight and pressure-tight manner up to a pressure of 70 bar. On the side of the base body 101 that faces the rear side of the dispensing device, one of the two rear gas conduits 135 opens in a hollow mandrel 136 that is open on both sides and has a passage. The second rear channel 135 opens into a drain channel 137 that is connected to the surroundings of the dispensing device through a sterile filter 138. Said drain channel can be used to release a gas pressure that is applied in the region of the cartridge connectors to the feed plunger of a connected cartridge (not shown). For this purpose, another passage (not shown) is arranged in the rotary valve body 110 and can be used, in appropriate position of the rotary valve body, to connect one of the openings 125 to the gas conduit 137. Additional sealing cams (not shown) are provided for closing the openings in the valve seat.

Three passages 112, 114 are arranged in the rotary valve body 110 and are offset along the axis of symmetry of the rotary valve body 110 and, in addition, are twisted with respect to each other about said axis of symmetry. The passages 112, 114 are arranged in the rotary valve body 110 in a manner and the gas conduits 130, 135, 137 are arranged in the base body 101 in a manner such that, in three positions of the rotary valve body 110 that can be adjusted through a rotation of the rotary valve body 110 in the valve seat with respect to the base body 101, the front gas conduit 130 is connected to a rear gas conduit 135, 137 each through one of the passages 112, 114 or the third passage (not shown), whereby all other gas conduits 130, 135, 137 are closed in pressure-tight manner by the sealing cams 116, 117, 118 of the rotary valve body 110. The width of the front opening towards the rotary valve body 110 that opens into the front gas conduit 130 is sufficient to allow each of the passages 112, 114 to be connected to the front gas conduit 130.

Alternatively, three front gas conduits 130 may be provided in the front part of the base body 101, whereby each front gas conduit 130 can be connected to a rear gas conduit 135, 137 through one passage 112, 114 each. In this case, each of the three front gas conduits 130 has a rear gas conduit 135, 137 and a passage 112, 114 assigned to it. A pressure relief valve that opens from a certain pressure can be arranged upstream of the sterile filters 138 and/or the sterile filter in the rotary valve body 110.

A key element (not shown) is arranged on a side of the rotary valve body 110 that projects from the base body 101 and is engaged by an operating element (not shown) having a matching counterpart for rotating the rotary valve 110 in the valve seat of the base body 101.

The mandrel 136 projects into a hollow space in the rear part of the base body 101 that is suitable for accommodating a gas cartridge 142. The purpose of the mandrel 136 is to open a gas cartridge 142 whose opening side is being pressed onto the mandrel 136. On the rear end of the hollow space, a locking device 144 is arranged on the inside, and fastening means 146 in the form of an external thread are arranged on the outside of the base body 101. The purpose of the locking device 144 is to prevent the closure cap 170 from being moved inadvertently. For this purpose, the locking device 144 can engage locking hooks 148 that are arranged on the closure cap 170. The purpose of the fastening means 146 is to connect the closure cap 170 to the base body 101 and, in the process, to push the gas cartridge 142 onto the mandrel 136, and to thus open it. For this purpose, fastening means 150 are provided on the closure cap 170 in the form of an internal thread.

The features of the invention disclosed in the preceding description and in the claims, figures, and exemplary embodiments, can be essential for the implementation of the various embodiments of the invention both alone and in any combination.

List of Reference Numbers

2 Jacket surface
4 Groove
6, 7, 30 Sealing cam
8, 9, 10, 22, 34 Opening
14, 18 Hollow space
16 Recess
20, 32, 112, 114 Feed-through
101 Base body
104 Cartridge connector having a large diameter
106 Cartridge connector having a small diameter
108 Pistol handle
110 Rotary valve body
116, 117, 118 Sealing cam
120, 121 Fixation device
125 Opening in the cartridge connector
130, 135 Gas conduit
136 Hollow mandrel
137 Drain channel
138 Sterile filter
142 Gas cartridge
144 Locking device
146 Fastening means
148 Locking hook
150 Fastening means
170 Closure cap

We claim:

1. A rotary valve body for a dispensing device that is arrangable in rotatable manner in a matching valve seat in the dispensing device, whereby the rotary valve body is rotationally symmetrical about the rotation axis of the rotary valve body at least within a region intended for the valve seat, and whereby at least one first sealing cam made of an elastic plastic material is arranged on the rotationally symmetrical jacket surface of said region and is raised above a radius of the rotationally symmetrical jacket surface such that the first sealing cam renders a circumference of the rotary valve body larger than an internal diameter of the valve seat, and whereby at least one feed-through is arranged in the rotary valve body and extends from a first opening in the rotationally symmetrical jacket surface of the rotary valve body in the region of the first sealing cam into a second opening in the rotationally symmetrical jacket surface of the rotary valve body, wherein the first sealing cam is arranged directly adjacent to the first opening at a distance from a front face of the rotary valve body that is the same distance as that between the first opening and the front face of the rotary valve body, wherein at least one second sealing cam made of an elastic plastic material is arranged on the rotationally symmetrical jacket surface and is raised above the radius of the rotationally symmetrical jacket surface such that the at least one second sealing cam renders the circumference of the rotary valve body larger than the internal diameter of the valve seat, and whereby at least a second feed-through is arranged in the rotary valve body, whereby the second feed-through extends from a third opening in the rotationally symmetrical jacket surface of the rotary valve body in the region of the second sealing cam into a fourth opening in the cover surface of the rotary valve body that is oriented outward with respect to the dispensing device, wherein the second sealing cam is arranged adjacent to the third opening at a distance from the front face of the rotary valve body that is the same distance as that between the third opening and the front face of the rotary valve body, wherein the first and second sealing cams are arranged to be diagonal with respect to each other and the first and third openings are arranged to be diagonal with respect to each other, wherein a first diagonal located between the first and third openings intersects a second diagonal located between the first and second sealing cams.

2. The rotary valve body according to claim 1, wherein an entire rotary valve body is made of more than 90% of at least one plastic material.

3. The rotary valve body according to claim 1, wherein the first sealing cam or sealing cams consist of polyoxymethylene, polyamide or polytetrafluoroethylene and the rotary valve body is also made of more than 90% polyoxymethylene, polyamide or polytetrafluoroethylene.

4. The rotary valve body according to claim 1, wherein the first opening is arranged at the same height, with respect to the rotary axis of the rotary valve body, as the first sealing cam, and, the third opening is arranged at the same height, with respect to the rotary axis of the rotary valve body, as the second sealing cam.

5. The rotary valve body according to claim 1, wherein the first feed-through extends through the rotary valve body such as to be perpendicular to the rotary axis of the rotary valve body such that the first opening becomes arranged opposite to the second opening.

6. The rotary valve body according to claim 1, wherein an axial hollow space is arranged in at least one of the cover surfaces of the rotary valve body and is open towards the outside, whereby a fourth opening is arranged in the hollow space, whereby the hollow space is arranged in the cover surface of the rotary valve body facing outward with respect to the dispensing device.

7. The rotary valve body according to claim 1, wherein at least two circumferential grooves are provided in the rotationally symmetrical jacket surface of the rotary valve body, whereby plastic guide rings are arranged in the grooves.

8. The rotary valve body according to claim 1, wherein the first opening and the third opening are offset with respect to each other by at least 10° relative to the rotation axis of the rotary valve body and are arranged at different height with respect to each other.

9. The rotary valve body according to claim 1, wherein the first sealing cam and the second sealing cam are offset with respect to each other by at least 10° relative to the rotation axis of the rotary valve body and are arranged at different height with respect to each other, whereby the first sealing cam is arranged at the same height with respect to the rotation axis as the first opening, the second sealing cam is arranged at the same height with respect to the rotation axis as the third opening , and the first and second sealing cams are offset with respect to the openings arranged at the same height by the same angle by which the first and second sealing cams are offset with respect to each other.

10. The rotary valve body according to claim 1, wherein the cover surface of the rotary valve body facing outwards with respect to the dispensing device has at least one key element arranged in it that is not symmetrical to the rotation axis of the rotary valve body such that the rotary valve body is rotatable in the valve seat by means of an operating element that engages the key element in form-fitting manner.

11. A medical spraying device or vacuum-generating device having the valve system according to claim 10 for regulating the gas flow.

12. A valve system comprising the rotary valve body according to claim 1 and a valve seat, in which the rotary valve body is supported such that the rotary valve body can rotate, whereby the first sealing cam or sealing cams of the rotary valve body are compressed by the valve seat.

13. The valve system according to claim 12, wherein the valve seat is manufactured from plastic material.

14. The valve system according to claim 13, wherein the plastic material is a thermoplastic material.

15. The valve system according to claim 12, wherein at least two openings opening into gas conduits are arranged in the valve seat, whereby the first sealing cam closes at least one opening in a first position of the rotary valve body in the valve seat and, in a second, rotated, position of the rotary valve body in the valve seat, the feed-through (20, 112) connects at least two openings such that a through-going gas conduit is formed.

16. The valve system according to claim 12, wherein at least three openings in the valve seat open into gas conduits, whereby the first sealing cam, in a first position of the rotary valve body in the valve seat, closes at least one opening and, in a second, rotated position of the rotary valve body in the valve seat, the feed-through connects at least two openings such that a through-going gas conduit is formed, and, in the first position, the third opening of the rotary valve body is connected to one of the at least three openings in the valve seat and, in the second, rotated position of the rotary valve body in the valve seat, the second sealing cam closes one of said at least three openings in the valve seat.

17. The rotary valve body according to claim 1, wherein the entire rotary valve body is completely made of plastic material.

18. The rotary valve body according to claim 1, wherein the rotary valve body and the first sealing cam or sealing cams are made up of a single part.

19. The rotary valve body according to claim 1, wherein the first and second diagonals intersect each other at a point of interception such that distances from the first and third openings to the point of interception and from the first and second sealing cams to the point of interception are equal in length.

20. The rotary valve body according to claim 1, wherein the first and second sealing cams are situated at an offset with respect to the first and third openings, respectively, by at least 10° but no greater than 20°, relative to the rotation axis of the rotary valve body.

\* \* \* \* \*